United States Patent
Clare

(10) Patent No.: US 6,916,301 B1
(45) Date of Patent: Jul. 12, 2005

(54) ELASTOMERIC WATERPROOF CAST AND BANDAGE COVER

(76) Inventor: Kenneth Clare, 13856 Paseo Cervera St., San Diego, CA (US) 92129

( * ) Notice: Subject to any disclaimer, the term of this patent is extended or adjusted under 35 U.S.C. 154(b) by 1106 days.

(21) Appl. No.: 09/624,406

(22) Filed: Jul. 24, 2000

(51) Int. Cl.$^7$ .................................................. A61F 5/00

(52) U.S. Cl. ........................................ 602/3; 128/856

(58) Field of Search ................................ 602/3, 4, 5, 8, 602/20, 21, 22; 128/845, 846, 849, 856

(56) References Cited

U.S. PATENT DOCUMENTS

| | | | | |
|---|---|---|---|---|
| 4,926,851 A | * | 5/1990 | Bulley | 602/60 |
| 5,592,953 A | * | 1/1997 | Delao | 128/882 |
| 5,761,746 A | * | 6/1998 | Brown | 2/243.1 |
| 6,126,621 A | * | 10/2000 | Aceves | 602/3 |

* cited by examiner

*Primary Examiner*—Michael A. Brown
(74) *Attorney, Agent, or Firm*—Fuess & Davidenas

(57) ABSTRACT

A waterproof cover for casts and/or bandages on limb extremities is formed as a thin-walled elastomeric water-impervious linear tube, preferably made of nitrile, open at at least one end. The cover stretches skin-tight over a limb extremity, and over any and all casts and/or bandages upon the limb extremity, so as to conform to a combined exterior contour of the limb and of any casts and bandages upon the limb. The cover circumferentially squeezes against the limb, sealing watertight both the limb and any casts and/or bandages upon the limb. The waterproof elastomeric tubular cover is comfortable, non-obtrusive, non-obstructive, and easily deployed, removed, and re-deployed. Preferred embodiments for use on the leg from the toes to the knee, and beyond to the thigh, range from 29 inches (73.5 cm.) to 41.0 inches (103.5 cm) in length, with a diameter at the ankle of 3.5 inches (8.9 cm); at the calf 5.0 inches (12.7 cm); and at the knee 4.5 inches (11.5 cm). Preferred embodiments for use on the arm from the fingertips to the elbow, and beyond to the arm pits, range from 16.0 inches (40.2 cm.) to 26.0 inches (65.5 cm) in length, with a diameter at the hand of 4.0 inches (10.1 cm); at the forearm 3.25 inches (7.7 cm); and at the biceps 10.0 inches (25.9 cm). Typically only four sizes suffice for 95+% of human usages.

2 Claims, 3 Drawing Sheets

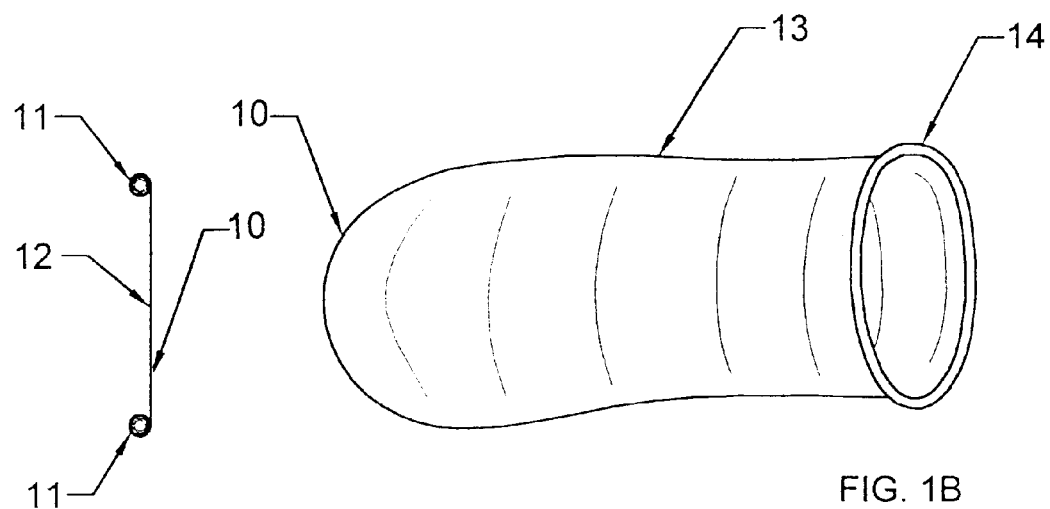
FIG. 1A
FIG. 1B
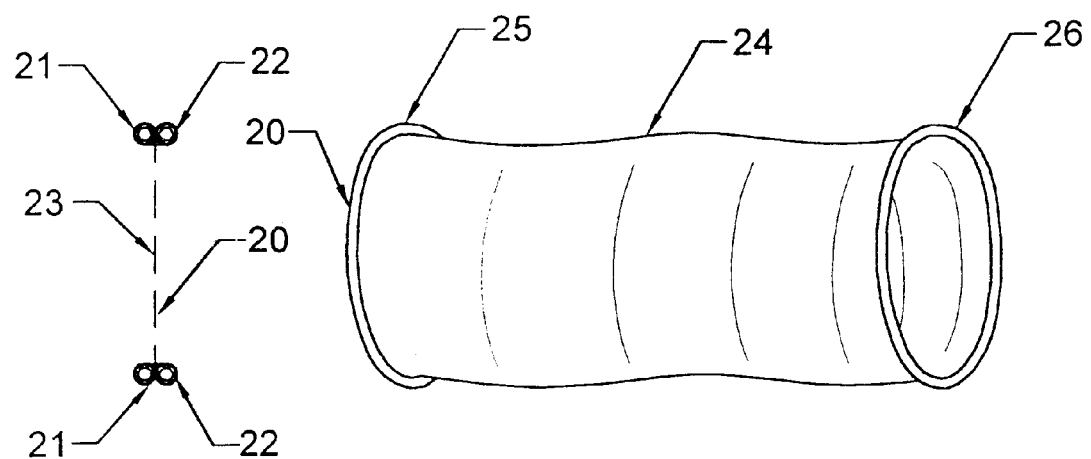
FIG. 2A
FIG. 2B

ELASTOMERIC WATERPROOF CAST AND BANDAGE COVER

BACKGROUND OF THE INVENTION

1. Field of the Invention

The present invention generally concerns covers, and waterproof covers, for casts and for bandages located on limb extremities so as to maintain dry the casts and bandages, preventing moisture from accumulating under the casts and bandages during exposure of the limb to water, such as during bathing, showering or swimming.

The present invention particularly concerns quick-deploying, easy-use, reusable, low-profile, snug-holding, comfortable, economical and operationally effective cast, bandage and dressing covers having the topologies of tubes open at one, or at both, ends.

2. Description of the Prior Art

The present invention will be seen to concern thin-walled, water-impermeable, cast and bandage covers that are entirely elastomeric, fitting snugly over and upon casts located on human limbs and limb extremities. Although cast and bandage covers of the prior art have occasionally had limited regions of elastic material, those prior art flexible cast covers known to the inventor are more commonly of an immutable topology of the nature of plastic bags than of the dynamic, stretch-fit, topology of condoms to which the present invention may be compared.

U.S. Pat. No. 4,301,603 to Scott for a WATER IMPERVIOUS BOOT FOR PROTECTING A SURGICAL CAST concerns a light weight flexible boot worn over a foot in a surgical cast to protect the cast from moisture. The boot has (i) a walking sole of tough rubber type material with a cushion sole and (ii) an upper body composed entirely of flexible and elastic foam material, with (iii) an inner fabric layer and (iv) an outer covering of water impervious fabric. The boot can be stretched over various sizes and shapes of casts. All joints in the boot are completely sealed and waterproof.

U.S. Pat. No. 4,363,317 to Broucek for a WATERTIGHT CAST COVER concerns a watertight cast cover for protecting a cast, bandage or the like. The cast cover includes an elongated, generally tubular waterproof member having a closed end and an open end. An adjustable resilient sealing band extends around the periphery of the open end of the member. The band includes overlapping ends, one end of which defines a flap. The flap and band may be stretched to form a seal with the user's limb, and the flap may be secured to the band.

U.S. Pat. No. 4,562,834 to Bates, et. al., for a WATERPROOF LIMB COVERING concerns a waterproof covering intended to be worn over a cast or bandage on an injured arm or leg. The covering comprises a generally tubular water-impervious sleeve which is closed at one end, and which has spaced cutting sites running from side to side along which the sleeve can be cut to different lengths. Apertured tabs are provided along the length of the covering to receive a strap for encircling the covering and sealing the covering around the limb, when the covering is cut at the cutting sites. Visual indicators identify the cutting sites. Additional seam segments serve to provide resistance to tearing at side edges.

U.S. Pat. No. 4,768,501 to George for a METHOD OF WATERPROOF SEALING OF CASTS AND DRESSINGS discloses a method of forming a waterproof seal about the cast or dressing on a patient. An air- and water-impervious flexible membrane is placed over the cast or dressing to a position where the membrane's edge margins overlie the patient's skin along the perimeter of the cast or dressing. A vacuum is created between the membrane and skin by evacuating air through a suction tube or valve. The vacuum creates a close, snug fit of the membrane over the entirety of the cast or dressing and over a relatively large surface area of skin to provide a waterproof seal.

U.S. Pat. No. 4,911,151 to Rankin, et. al. for a DISPOSABLE DRESSING COVER concerns a disposable waterproof covering for a cast or bandage on an arm or leg. The cover is used primarily when bathing or showering to protect against wetting the cast or bandage. A generally tubular plastic sleeve is sealed to the user's arm or leg above the cast or bandage by a flexible plastic strap to effect a snug, water-tight, contact of the sleeve with the arm or leg. The strap is secured by an adhesive at one end to the sleeve adjacent the open end of the sleeve, and is wound around 360 degrees and secured at its other by a pressure-sensitive adhesive.

U.S. Pat. No. 4,986,265 to Caponi for a PROTECTIVE COVER FOR CAST concerns a protective cover for covering a plaster cast or the like on a patient. The cover includes an elongated waterproof, flexible, polymer bag having an opening in one end. The open end of the polymer bag has a surrounding elastic edge to hold the elongated, waterproof, flexible, polymer bag over a cast on a patient's limb. A small piece of hook and loop material is attached to the flexible bag. An elongated, substantially flat sealing band is made of an elastic, resilient, waterproof foamed polymer material with hook and loop material attached thereto. The hook material is positioned at predetermined positions on one side of the flat sealing band while the other side of the sealing band is covered with a loop. The elongated, waterproof, flexible, polymer bag is placed over a cast and the elongated, substantially flat sealing band attached on one end to the piece of hook and loop material on the bag. The sealing band is then wrapped around the open end of the bag to form multiple, overlapping, wrappings. The wrappings seal the open end of the bag against the intrusion of liquid when the sealing band is both stretched to form a tight seal and attached with the hook and loop material.

U.S. Pat. No. 5,016,648 to Brown, et. al., for a LIMB PROTECTIVE COVERING concerns a tubular sleeve of waterproof material for receiving a limb and an elongated closure member for tightening this sleeve around the limb. A portion of the sleeve above the closure member is folded over the closure member to form a cuff. A belt attaches to the cuff and wraps around the cuff to completely seal the covered limb.

U.S. Pat. No. 5,342,286 to Kelly, et. al., for a WATERPROOF COVERING describes a water-impervious covering for the extremities. The covering is intended to protect a bandage or cast portion of the extremity during bathing or the like. The covering is a sack-like member having an upper lip extending above the opening in the covering. The lip has a laterally extending perforation parallel to the opening extending approximately four-fifths of the width thereof. An adhesive strip extends the entire width of the lip from one side to the other. The adhesive strip is covered with a protective removable sheet. In use, the perforation is torn to separate the lip into a tie member and a securing member. The adhesive protective sheet is then removed and the extremity inserted into the sack-like covering. The securing portion then is adhered to the surface of the extremity and the opening gathered around the extremity so that the tie member may be used to encircle the gathering and thereby secure the covering to the extremity.

U.S. Pat. No. 5,395,302 to Botha, et. al., for a PROTECTIVE SHEATH FOR AN INJURED LIMB concerns a limb sheath used to provide a waterproof cover for an injured limb, such as a burned limb or a limb which is bandaged or in a cast. The sheath has a water impervious sleeve made of a first plastics material. The sleeve has an open end through which a limb can be inserted. A sealing strip is fastened to and extends about the internal surface of the sleeve at the open end. The sealing strip is made of a second plastics material which is more highly plasticized than the first plastics material. There is also an elastic strap which is connected to and extends from the sleeve adjacent the open end. The strap is fastened to itself by mating components of a self-contact fastener. In use with the sealing strip in contact with the limb, the strap can be stretched resiliently, wrapped about the open end and fastened to itself, thereby pressing the sealing strip against the limb to form a water-tight seal at the open end.

U.S. Pat. No. 5,643,183 to Hill for a WATERPROOF COVER FOR CASTS AND BANDAGES discloses a waterproof cover for casts and bandages on the extremities. The cover includes an elongated sleeve of transparent polyethylene having a thickness between about 0.001 and 0.006 inches and a length greater than its width. The sleeve has a face side and an obverse side and a distal end and a proximal end. It is hermetically sealed at its distal end thus forming a waterproof cover. A hook and loop fastener is used for affixing the cover on the extremity. A first strip of the hook and loop fastener is disposed on the proximal end of the face side of the sleeve, the first strip having an array of plastic hooks disposed thereon. The first strip extends substantially across the entire width of the face side and the hooks face outwardly from the sleeve. A second strip of loops is disposed on the proximal end of the obverse side. A covering of soft fleece is disposed on the face side. The second strip has a length greater than the width of the sleeve whereby to form extensions to engage the hooks on the first strip. The second strip is joined to the obverse side at its middle thereby leaving the distal ends of the second strip to be unrestricted in movement and to allow portions of the obverse side to be folded and gathered within the sleeve and secured in place by the second strip, thereby to form a water resistant cover when placed upon an extremity.

U.S. Pat. No. 5,728,052 to Meehan for a WATERPROOF ENCLOSURE concerns a waterproof enclosure including a pliable, waterproof, elongated sheath having either (i) a closed end and an open end, or (ii) two open ends. A resilient, waterproof, sealing element is associated with each open end. A pliable, waterproof, bellows car be interposed between and contiguous with (i) the end of each sealing element and (ii) the sheath. Each sealing element may include a first end that is of smaller diameter than a second end, a frustaconical shape, and/or ribs. A closed sheath end may have a rough surface to improve traction. A gas passage through the sheath can be provided that includes a port activated from a first state for inhibiting gas movement through the gas passage and a second state for permitting gas movement through the gas passage. The port can be manually movable from the first state to the second state, and can include a pressure relief valve. The waterproof enclosure can include a loop integral with the exterior surface of the sheath to which an elasticized cord may be attached. An apertured covering that encloses at least a portion of the waterproof enclosure is also disclosed.

SUMMARY OF THE INVENTION

The present invention contemplates stretchable covers for casts, bandages, dressings and the like located on human limbs and limb extremities. The stretchable covers are waterproof, quick-deploying, easy-use, reusable, low-profile, snug-holding, comfortable, economical and operationally effective when applied to protect the casts, bandages, dressings and the like.

The contemplated covers realize these benefits by dint of being (i) entirely elastomeric; and, as delivered into service rolled, (ii) easily unrolled onto a limb and into a deployed position over any cast, bandage, dressing or the like; and (iii) equally easily rolled off the limb and stored, including for reuse if desired.

In one of its aspects the present invention is embodied in a limb shield made from a waterproof thin-walled substantially linear elastomeric tube that is (i) open at at least one end, (ii) delivered into service with a substantial body of the tube rolled into an annular ring, and (iii) sized and adapted to unroll over a portion of a human limb and any cast, bandage, dressing on the limb so as to thereafter circumferentially conform to, squeeze and seal watertight this portion of the limb.

In one preferred, first, embodiment of the limb shield the elastomeric tube (i) is open at one end only, having a topology of a condom. Moreover, it preferably unrolls upon the limb in a like manner as a condom unrolls upon the penis. Moreover, it preferably assumes when unrolled a deployed position upon the limb like as to the position assumed upon the penis by a condom. In its preferred form the unrolled deployed elastomeric tube is everywhere snug to the limb, and interferes but minimally with usage of the limb.

The elastomeric tube of the limb shield is preferably somewhat longer than the lineal extend of the portion of the limb upon which it is intended to fit, and which it is intended to cover. When the tube is unrolled and is deployed upon the limb in the manner of the condom, then an unrolled portion of the tube will remain rolled within the annular ring. This unrolled portion of the annular ring will squeeze and seal watertight against the limb relatively more strongly at the open end of the tube than at remaining regions of the tube that are then unrolled upon the limb. The unrolled and deployed tube is thus most strongly watertight to the limb at an entrance to its open end—exactly where desired!

In a variant to this first embodiment, the tube of the limb shield is sized and adapted to fit over a forearm and hand from tips of the fingers to, depending upon the extent unrolled, a terminus circumferentially around the arm (i) below, (ii) at, or (iii) above the region of the elbow. By this construction at least the forearm, if not also the elbow and a portion of the upper arm, is squeezed and shielded watertight by deployment of the limb shield.

In another variant to this first embodiment, the tube of the limb shield is sized and adapted to fit over a lower leg and foot from tips of the toes to, depending to the extent unrolled, a terminus circumferentially around the leg at the region (i) below, (ii) at, or (iii) above the knee. By this construction at least a portion of the lower leg, and even the knee and the complete leg to the hip, is squeezed and shielded watertight by deployment of the limb shield.

In another, less-preferred, second embodiment of the limb shield the elastomeric tube is open at both ends, having the topology of tube, or straw.

The tube is preferably longer than a lineal extent of the limb that it is intended to cover. It is preferably delivered into service rolled, roughly equally, from both open ends of the tube into two side-by-side rolled annular rings. So rolled, the tube is first placed upon the limb, and over any cast, bandages or dressings upon the limb, roughly centrally to a region of the limb that the tube is intended to cover. The annular rings of the rolled tube may be, for example, stretched with the hands and fingers and positioned upon the limb. One positioned, one rolled annular ring is unrolled in one direction and the other annular ring is unrolled in the other direction. The unrolling of the tube in two opposite directions serves to cover the intended region of the limb.

The length of the tube may be preset so that a portion of both ends of the rolled tube will remain rolled in the annular ring after deployment. These two end portions of the tube, remaining rolled, will, by dint of the extra elastomeric material of the tube existing at these portions, squeeze tightly against parts of the limb then located within the open end or ends of the tube, sealing watertight the tube at its ends particularly well. If one end of the open tube is not located about the limb—as might be the case during emergency use of a leg shield upon the forearm, or an adult-sized shield upon a child—then it is a straightforward matter to tie off the open end, in the manner of a balloon.

In one variant to this second embodiment, the tube of the limb shield is sized and adapted to unroll to a varying extent so as to fit over a forearm from the wrist to regions (i) below, (ii) at, or (iii) above the elbow. By this construction at least the forearm, if not also the elbow and/or a portion of the upper arm, is squeezed and shielded watertight.

In another variant to this second embodiment, the tube of the limb shield is sized and adapted to unroll to a varying extent so as to fit over an upper arm from regions (i) below, (ii) at, or (ii) above the elbow to regions (i) below or (ii) at the shoulder. By this construction a portion of the upper arm is squeezed and shielded watertight.

In yet another variant to this second embodiment, the tube of the limb shield is sized and adapted to unroll to a varying extent so as to fit over a lower leg from regions (i) below, (ii) at, or (iii) above the ankle to regions (i) below, (ii) at, or (ii) above the knee. By this construction a portion of the lower leg is squeezed and shielded watertight.

In still yet another variant to this second embodiment, the tube of the limb shield is sized and adapted to unroll to a varying extent so as to fit over an upper leg from regions (i) below, (ii) at or (iii) above the knee to regions of the upper leg near the hip or crotch. By this construction a portion of the upper leg is squeezed and shielded watertight.

In still yet another variant to this second embodiment, the tube of the limb shield is sized and adapted to fit over portions of the foot and lower leg from the regions near the toes to regions near the knee. By this construction toes, and optionally also the knee, may be left exposed by a shield substantially centered about the ankle.

In each of these first and second embodiments, and in each of these variants, the limb shield is preferably sized and adapted to fit not only over a limb, but also over any cast, bandage, dressing, medical monitor or the like that may be positioned upon the limb, circumferentially squeezing and conforming to the contours of the combined limb and anything upon the limb. It will be understood that the unrolled deployed elastomeric tube is everywhere snug to the cast upon the limb, and minimally interfering with usage of the limb—as is uncommon in the prior art.

In another of its aspects the present invention may be considered to be embodied in a waterproof cover for casts and bandages on limb extremities.

The cover is formed as a thin-walled elastomeric water-impervious linear tube, open at least one end, stretching skin-tight over a limb extremity and any and all casts and bandages upon the limb extremity so as to (i) conform to a combined exterior contour of the limb and of any casts and bandages upon the limb, (ii) circumferentially squeezing against the limb and (iii) sealing watertight the limb and any casts and bandages upon the limb.

This tube, once deployed upon the limb, may be non-destructively removed from the limb by rolling up the tube, while the tube remains stationary and non-sliding upon the limb, so as to take up the tube into, and so as to form, a rolled annular ring.

Moreover the tube, once taken up into the rolled annular ring, may subsequently be re-deployed by unrolling the rolled annular ring onto the limb.

Finally, in yet another of its aspects the present invention may be considered to be embodied in a method of deploying and re-deploying a waterproof cast and bandage cover for a limb upon which is present a cast, a bandage, a dressing, or a medical appliance or the like.

The method consists of first unrolling a thin-walled elastomeric water-impervious linear tube onto a limb so that the unrolled tube squeezes circumferentially against the limb and seals watertight against the limb and any casts and bandages upon the limb. Then, at a desired time after first unrolling, the tube is re-rolled from off the limb. While doing so the tube remains stationary, and non-sliding, upon the limb. The re-rolling takes up the tube into, and forms, a rolled annular ring. Finally, at a desired time after re-rolling, the thin-walled elastomeric water-impervious linear tube is unrolled again onto the limb. The unrolled tube again squeezes circumferentially against the limb and seals watertight against the limb and any items upon the limb. The unrolling, the re-rolling, and unrolling clearly collectively constitute the deploying, and a re-deploying, of a reusable tube.

If wet, the exterior surface of the tube is preferably dried before re-rolling.

These and other aspects and attributes of the present invention will become increasingly clear upon reference to the following drawings and accompanying specification.

BRIEF DESCRIPTION OF THE DRAWINGS

FIG. 1a is a cut-away side view showing a first, single closed end, embodiment of an elastomeric waterproof cast and bandage cover in accordance with the present invention.

FIG. 1b is a diagrammatic perspective view showing the first embodiment of an elastomeric waterproof cast and bandage cover in accordance with the present invention also seen in FIG. 1a.

FIG. 2a is a cut-away side view showing a second, double open end, embodiment of an elastomeric waterproof cast and bandage cover in accordance with the present invention.

FIG. 2b is a diagrammatic perspective view showing the second embodiment of an elastomeric waterproof cast and bandage cover in accordance with the present invention also seen in FIG. 2a.

DESCRIPTION OF THE PREFERRED EMBODIMENT

Figure 3A:
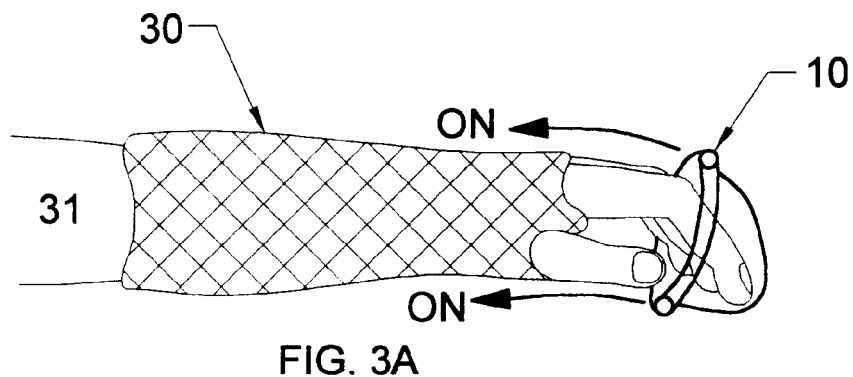
FIG. 3, consisting of FIGS. 3a through 3d, are diagrammatic perspective views showing the placement, and the removal, of the first embodiment of an elastomeric waterproof cast and bandage cover in accordance with the present invention, previously seen in FIGS. 1a and 1b, over a cast upon a patient's forearm.

A first embodiment of an elastomeric waterproof cast and bandage cover 10 in accordance with the present invention is shown in cut-away side view in FIG. 1a, and in diagrammatic perspective view in FIG. 1b. The cover 10 is made of a th n, flexible and elastomeric material that is most typically transparent or translucent. It is preferably made from nitrile, also know as nitrile butyl rubber, or NBR. As different patient applications and usages demand, the cover 10 can be made in various thicknesses and elastic strengths from (i) a few mils thickness of nitrile as might best suit use as a bathing shield for a woman or small child to (ii) over ten (1) mils thickness of butyl rubber as might best suit a weather and dirt shield to the limb cast or bandage of a rugby player. The preferred thickness, suitable for virtually all applications from smallest children to grown men working in construction and other vigorous activities, is six (6) mils.

The cover 10 bi-directionally both rolls and un-rolls, in the manner of a condom, between the rolled position of FIG. 1a and the unrolled position of FIG. 1b. In the rolled position of FIG. 1a the substantial material of the cover 10 is taken up into an annular peripheral ring 11 that is spanned and connected by a single thickness circle 12 of the material. In the unrolled position of FIG. 1b the substantial material of the cover 10 extends as the closed-end tube 13 while an end-opening 14 still presents and annular ring 14, the remnant of annular ring 11, in which, most typically, several thicknesses of material are still rolled.

A second embodiment of an elastomeric waterproof cast and bandage cover 20 in accordance with the present invention is shown in cut-away side view in FIG. 2a, and in diagrammatic perspective view in FIG. 2b. The cover 20 is suitably made of the same materials as is the cover 10 shown in FIG. 1. However, topologically the cover 20 is a double open-ended tube (or other prism).

As with the cover 10, the cover 20 also bi-directionally both rolls and un-rolls between the rolled position of FIG. 1a and the unrolled position of FIG. 1b. The cover 20 and be completely rolled to either one of its two ends. However, the rolling is normally, preferably, from both ends roughly equally until the rolled cover 10 assumes the position shown in side view in FIG. 2a. Namely, the cover 20 is taken up into two annular peripheral rings 21, 22 jointly containing the substantial material of the cover. The rolled layers of the annular rings 21, 22 are spanned and connected by a single thickness circle 23 of the material.

In the unrolled position of FIG. 2b the substantial material of the cover 20 extends as the double-open-ended tube 24 while each of the two end-openings still respectively present an annular ring 25, 26 which annular rings 25, 26 are the respective remnants of the annular rings 21, 22.

Each of the covers 10, 20 most typically comes in various sizes distinguished by both (i) length and (ii) diameter, depending upon intended application. As is known in human ergonomics, the length of the fingers to the elbows varies from roughly 5½" in infants to 8" in children to 13" in adolescents to 14" through 18" in small through large adults (males generally being larger). The corresponding distances from the fingertips to the mid region of the upper arm varies from roughly 8½" in infants to 12" in children to 20½" in adolescents to 23" through 26" in small through large adults (males generally being larger). If a cover 10, 20 intended for use in regions of the hand and arm is fabricated to one only length, then this length is most typically 24". Normally the covers 10, 20 are fabricated in number of lengths, see below.

As is also known in human ergonomics, the length of the toes to the knees varies from roughly 4½" in infants to 11½" in children to 17½" in adolescents to 18" through 24" in small through large adults (males generally being larger). The corresponding distances from the toes to the mid region of the upper leg varies from roughly 10" in infants to 18" in children to 26½" in adolescents to 32' through 33" in small through large adults (males generally being larger). If a cover 10, 20 intended for use in regions of the toes and/or feet, and legs, is fabricated to one only length, then this length is most typically 30". Normally the covers 10, 20 are fabricated in number of lengths, see below.

Each of the covers 10, 20 most typically comes in four sizes variously primarily suitable to cover (i) the leg from the toes to the knee, (ii) the leg from the toes co the crotch, (iii) the arm from the fingertips to the elbow, and (iv) the arm from the fingertips to the shoulders.

The embodiment for (i) the leg from the toes to the knee, including coverage of the foot, is 29 inches (73.5 cm.) long. The diameter at the ankle is 3.5 inches (8.9 cm); at the calf 5.0 inches (12.7 cm); and at the knee 4.5 inches (11.5 cm). Circumference at the ankle is 9.0 inches (22.9 cm); at the calf 13.0 inches (33.0 cm); and at the knee 12.5 inches (31.7 cm).

The embodiment for (ii) the leg from the toes to the crotch or thigh, including coverage of the foot, is 41.0 inches (103.5 cm) long. The length of the portion from knee to thigh is 13.0 inches (32.5 cm). The diameter at the thigh is 6.25 inches (15.4 cm); at the region from above the knee to the thigh 4.50 Inches (11.5 cm). The circumference at the region above the knee is 14.0 inches (35.1 cm) increasing to 19.0 inches (47.6 cm) at the thigh.

The embodiment for (iii) the arm from the fingertips to the elbow is 16.0 inches (40.2 cm) long.

The embodiment for (iv) the arm from the fingertips to the shoulders, or arm pit, is 26.0 inches (65.5 cm) long. For these arm embodiments the diameter at the hand is 4.0 inches (10.1 cm); at the forearm 3.25 inches (7.7 cm); and at the biceps 10.0 inches (25.9 cm). The circumference at the hand is 9.25 inches (22.9 cm); at the wrist 6.0 inches (14.7 cm); at the forearm 9.38 inches (23.6); and at the biceps 10.5 inches (26.3 cm).

The preferred thickness of all embodiments is from 2 to 10 mils, and is most preferably 5–1 mils. The greater thicknesses are associated with the longer covers 10, 20.

Accordingly, variously sized covers 10, 20 are suitable for protective use over limbs ranging in size from those of small children to adult males. Although the smaller diameter covers 10, 20 are typically also somewhat shorter, reduction in length with decrease in diameter (or vice versa) is not mandatory. Covers 10, 20 may be used on something as short as the wrist cast of a child (about 6 inches long) to something as long as the full foot, leg and thigh cast of a tall man (perhaps 48" long).

The principle that permits a limited number of sizes to suit all applications is simple. A cover 10, 20 is chosen to be in various of its regions of various diameters each of which is slightly less than the narrowest diameter of the corresponding region of the limb that it will cover. Meanwhile, any unused length when the cover 10, 20 is placed upon a limb extremity (which unused length may be considerable) is simply not unrolled.

Typical applications of elastomeric waterproof cast and bandage cover of the present invention, particularly and by way of example the first embodiment cover 10, are shown in diagrammatic perspective view in FIGS. 3 and 4.

Figure 3B:
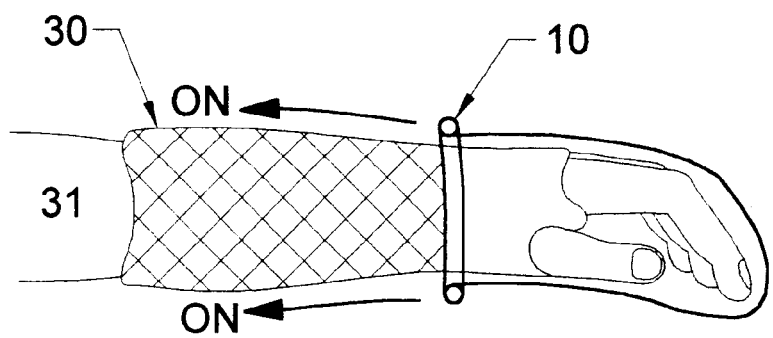
Figure 3C:
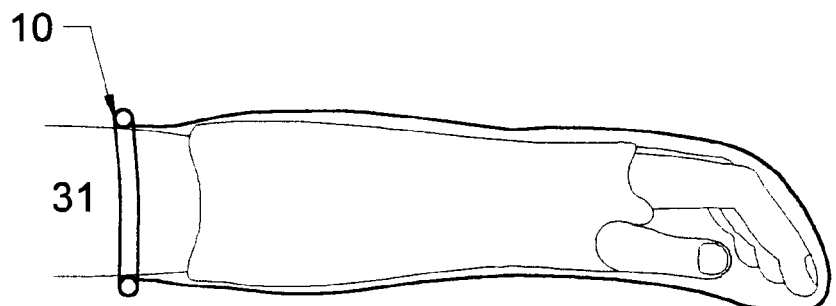
Figure 3D:
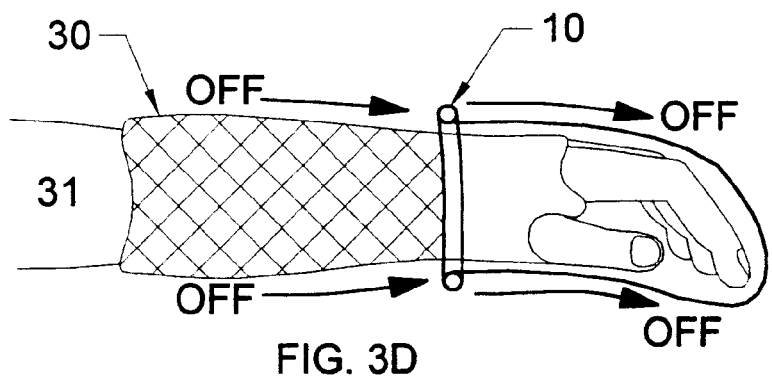

A placement of the first embodiment 10 of an elastomeric waterproof cast and bandage cover over a cast 30 upon a patient's arm 31 is shown in the sequence of FIGS. 3a–3c. Unrolling of the cover 10 is in the direction of the arrows "ON". The removal of the same first embodiment cover 10 of an elastomeric waterproof cast and bandage cover from about the same cast 30 upon the same patient's arm 31 is shown in FIG. 3d. Removal preferably transpires by re-rolling the cover 10 in the direction of arrows "OFF".

In the placement of FIG. 3 the embodiment 10, being an elastomeric tube open at one end only in the topology of a condom, unrolls upon the patient's arm 31 and cast 30 in a like manner as a condom unrolls upon the penis. So unrolled the embodiment 10 assumes a deployed position upon the patient's arm 31 like as to the position assumed upon a penis by a condom. Namely, the unrolled deployed elastomeric tube is everywhere snug to the limb, while minimally interfering with usage of the limb.

The tube is preferably longer than the portion of the limb in FIG. 3 the lower portion of the patient's arm 31—that it is intended to cover, making that when the tube is unrolled and is deployed upon the limb in the manner of the condom then an unrolled portion of the tube will remain rolled within an annular ring 14 (also shown in FIG. 1b). This unrolled portion within the annular ring 14 will squeeze and seal watertight against the limb, or patient's arm 31, relatively more strongly at the open end of the tube than at remaining regions of the tube that are then unrolled upon the limb. Accordingly, the unrolled and deployed tube is most strongly watertight to the limb at an entrance to its open end—exactly what is wanted.

In FIG. 3 the first embodiment cover 10 of the present invention is sized and adapted to fit over a forearm and hand from tips of the fingers to a terminus circumferentially around the patient's arm at the region of the patient's elbow, all as illustrated. In this position the patient's forearm is squeezed and shielded watertight by deployment of the cover, or limb shield, 10.

Figure 4A:
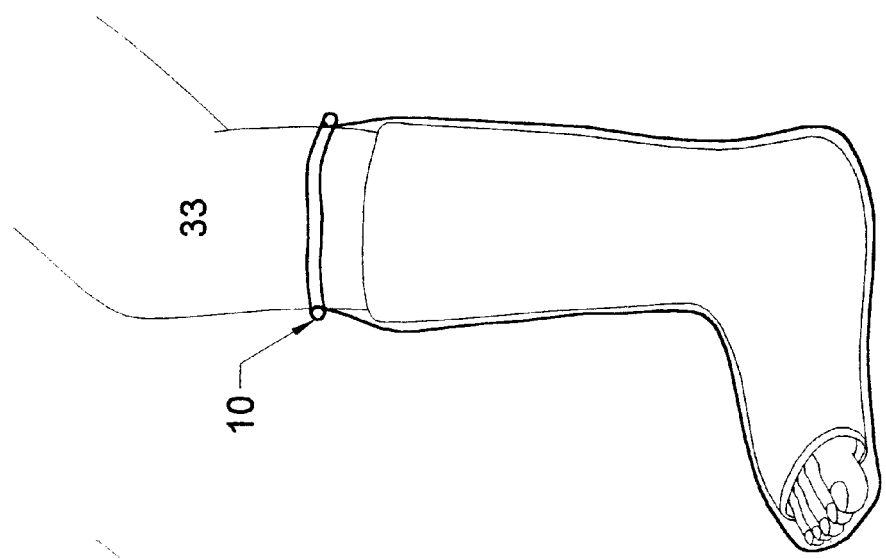
FIG. 4, consisting of FIGS. 4a through 4c, are diagrammatic perspective views showing the placement of the first embodiment of an elastomeric waterproof cast and bandage cover in accordance with the present invention, previously seen in FIGS. 1a and 1b, over a cast upon a patient's lower leg.
Figure 4B:
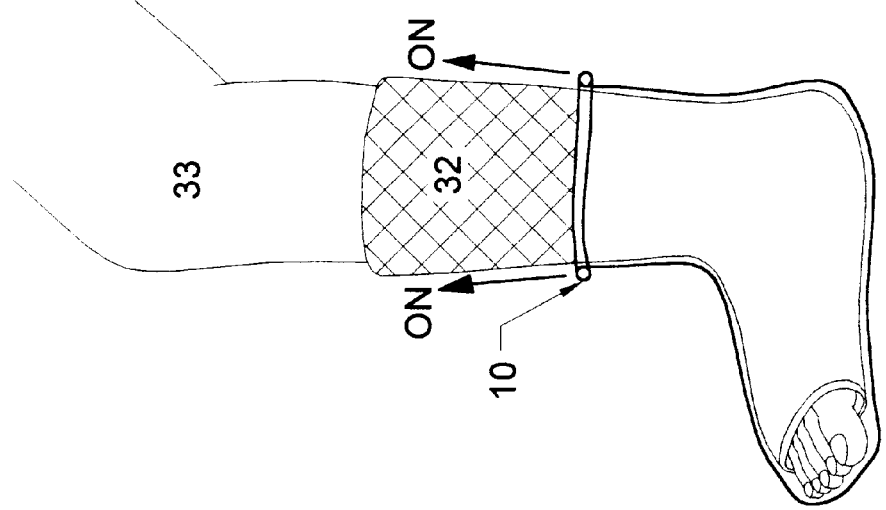
Figure 4C:
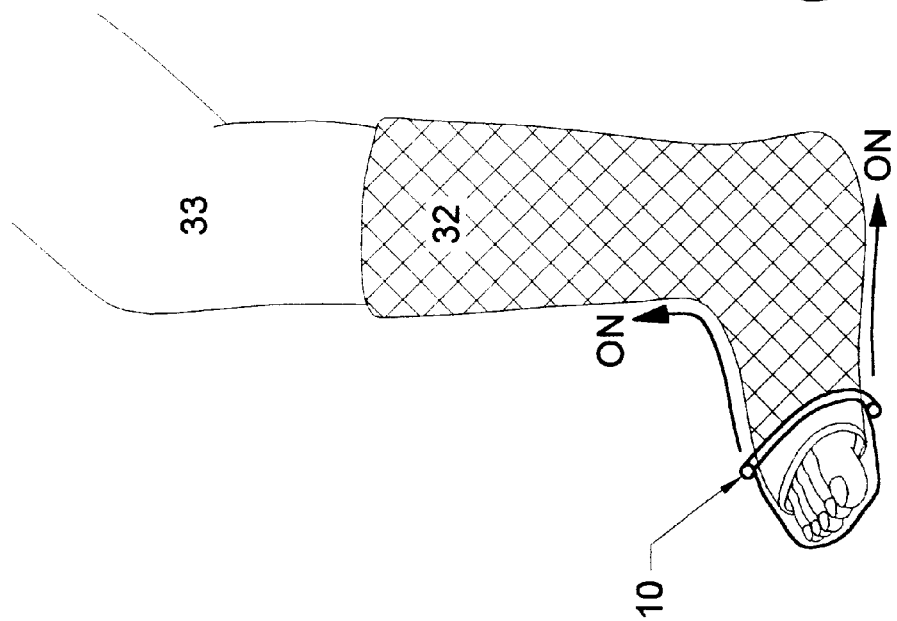

An alternative placement is shown in FIG. 4, consisting of FIGS. 4a through 4c. Here the cover, or limb shield, 10 in accordance with the present invention is sized and adapted to fit over a patient's lower leg and foot from tips of the toes' to a terminus circumferentially around the leg at the region of the knee. In this position the patient's lower leg is squeezed and shielded watertight by deployment of the cover, or limb shield, 10.

Placement of the first embodiment 10 of an elastomeric waterproof cast and bandage cover over a cast 32 upon a patient's leg 33 is shown in the sequence of FIGS. 4a–4c. Unrolling of the cover 10 is in the direction of the arrows "ON". The removal of the same first embodiment cover 10 of an elastomeric waterproof cast and bandage cover from about the same cast 32 upon the same patient's leg 33, not shown, is accomplished in an analogous to the showing of FIG. 3d. Removal again preferably transpires by re-rolling the cover 10.

Deployments of the second embodiment 20 of the cover, or limb shield, of the present invention are not shown, but operated equivalently to the first embodiment shown in FIGS. 3b and 4b. It will be recalled that the second embodiment 20, shown in FIG. 2, is open at both ends, having the topology of a straw.

In application, either embodiment of the cover, or limb shield, 10, 20 in accordance with the present invention is longer than a lineal extent of the limb that it is intended to cover. The tubular body of the cover 10 is delivered into service rolled from one end, as is best shown in FIGS. 3a and 4a. The tubular body of the cover 20 is delivered into service rolled from both ends, roughly equally, dividing the tube into two side-by-side rolled annular rings, as shown in FIG. 2a. This dictates that the cover 20 be initially placed upon the limb roughly centrally to a region of the limb that the cover 20 is intended to protect. Then one rolled annular ring is unrolled in one direction and the other annular ring is unrolled in the other direction. This unrolling of the tube in two opposite directions serves to cover the intended region of the limb.

By this manner of deployment a portion of both ends of the rolled tube will remain rolled in the annular rings 25, 26 (also seen in FIG. 2b), and these annular ring rolled portions 25, 26 will, by dint of the extra elastomeric material of the tube existing at these end portions, seal watertight particularly well against parts of the limb then located within the open ends of the tube.

For example, in FIG. 3b a cover 10 sized and adapted to fit over a forearm from the wrist to the elbow squeezes and shields watertight the patient's forearm. Of course, if the cover 10 were to be replace with a cover 20, then it might serve to also squeezed and shield watertight the patient's wrist, or hand.

In illustration of sizing to fit the intended use, in FIG. 4 a cover 10 is sized and adapted to fit over a patient's lower leg from the ankle to the knee. In this position it squeezes and shields watertight the patient's lower leg. Of course, if the cover 10 were to be unrolled still further, then it might extend so far as to squeeze and shield watertight the patient's knee, and even a lower portion of the patient 's upper leg even so far as the hip or crotch.

No matter where fitted and deployed, it should always be understood that a cover, or limb shield, in accordance with the present invention is both (i) sized and adapted to fit not only over a limb, but also over any cast or bandage(s) upon the limb, circumferentially squeezing and conforming to the contours of the cast or bandage(s), and (ii) so deployed, is everywhere snug to the cast and/or bandage(s) upon the limb, and to the limb itself. This is a great advantage of the present invention over prior art cast covers in that the elastomeric tubes of the present invention may not only be fitted, removed, and refitted easily, but, when deployed, are, in accordance with their modest thickness and snug fit everywhere, minimally interfering with use of the limb.

The covers of the present invention are thus particularly useful for shielding limbs and limb extremities during participation in sports or other activities where contamination is desired to be avoided but where free movement, with minimum surplus material subject to be snagged or ripped, is desired to be enhanced.

In accordance with the preceding explanation, variations and adaptations of the elastomeric waterproof cast and bandage cover in accordance with the present invention will suggest themselves to a practitioner of the medical device design arts. For example, all sorts of practical and decorative indicia can be placed upon the covers without departing from the spirit of the invention. It must not be thought that the covers are solely usable for medical purposes: they can be donned when handling, or walking in, injurious or distasteful material, such as poison ivy or barnyard excrement. The covers can be deployed in layers one over the top of the next both for added security in protection, and for the ability to "peel one off" if damaged or contaminated. The covers can be made—normally by the simple addition of food starch to the matrix of the nitrile, plastic or rubber—to be biodegradable, including as might be flushed down a toilet.

In accordance with these and other possible variations and adaptations of the present invention, the scope of the invention should be determined in accordance with the following claims, only, and not solely in accordance with that embodiment within which the invention has been taught.

What is claimed is:

1. A method of deploying and re-deploying a waterproof cast and bandage cover for a limb upon which is present a cast, a bandage or both a cast and a bandage, the method comprising:

first unrolling a thin-walled elastomeric water-impervious linear tube onto a limb so that the first unrolled tube squeezes circumferentially against the limb and seals watertight against the limb and any casts and bandages upon the limb; and then, at a desired time after first unrolling, re-rolling the tube from off the limb, while the tube remains stationary and non-sliding upon the limb, so as to take up the tube into, and so as to form, a rolled annular ring; and then, at a desired time after re-rolling, second unrolling the thin-walled elastomeric water-impervious linear tube again onto the limb so that the second unrolled tube again squeezes circumferentially against the limb and seals watertight against the limb and any casts and bandages upon the limb, wherein the first unrolling, the re-rolling, and the second unrolling collectively constitute a deploying, and a re-deploying of the tube, which tube serves as a waterproof cast and bandage cover.

2. The method according to claim 1 that, between the first unrolling and the second unrolling, comprises:

getting the first-unrolled deployed tube wet on its exterior surface, an interior surface of the tube and the limb and any casts and bandages upon the limb remaining dry; and rendering dry the exterior surface of the wet first-unrolled deployed tube so that the tube may be re-rolled while dry.

* * * * *